(12) United States Patent
Casutt et al.

(10) Patent No.: US 7,073,415 B2
(45) Date of Patent: Jul. 11, 2006

(54) INSTRUMENT SYSTEM FOR PEDICLE SCREWS

(75) Inventors: Simon Casutt, Gossau (CH); Nimrod Meier, Schaffhausen (CH); Marc Huber, Turbenthal (CH)

(73) Assignee: Centerpulse Orthopedics Ltd. (CH)

( * ) Notice: Subject to any disclaimer, the term of this patent is extended or adjusted under 35 U.S.C. 154(b) by 88 days.

(21) Appl. No.: 10/829,123

(22) Filed: Apr. 21, 2004

(65) Prior Publication Data

US 2005/0010220 A1    Jan. 13, 2005

(30) Foreign Application Priority Data

Apr. 24, 2003 (EP) .................................. 03009326

(51) Int. Cl.
*B25B 23/08* (2006.01)

(52) U.S. Cl. ..................... 81/451; 81/459; 606/104

(58) Field of Classification Search .................. 81/451, 81/437–439, 459, 461; 606/104
See application file for complete search history.

(56) References Cited

U.S. PATENT DOCUMENTS 5,941,885 A * 8/1999 Jackson ...................... 606/104
6,235,028 B1 5/2001 Brumfield et al.
6,251,112 B1 6/2001 Jackson

FOREIGN PATENT DOCUMENTS

| DE | 100 05 134 A1 | 8/2001 |
|---|---|---|
| EP | 0 669 101 B1 | 8/1995 |
| EP | 0 669 109 B1 | 8/1995 |
| EP | 1 103 225 A2 | 5/2001 |
| FR | 2 703 288 A1 | 10/1994 |

* cited by examiner

*Primary Examiner*—Debra S Meislin
(74) *Attorney, Agent, or Firm*—Christie, Parker & Hale, LLP.

(57) ABSTRACT

The invention relates to an instrument system for pedicle screws having a thread in their head which has a clamping screw in the direction of their screw axes, which can be actuated by a power screw driver, with holders for the absorbing of a torque contacting the head of the pedicle screw in a shape matched manner. Since the holders have a tubular part which is coordinated with its inner diameter to the guiding of the clamping screw and with centring parts being able to be fastened in the heads of the pedicle screws instead of the clamping screws, said pedicle screws being engageable when the holder is mounted on, the contact to the inserted pedicle screw can also be maintained with a non visible, i.e. smaller operation field, in order mount the same holder or other holders a plurality of times.

12 Claims, 6 Drawing Sheets

INSTRUMENT SYSTEM FOR PEDICLE SCREWS

CROSS REFERENCE TO RELATED APPLICATION

This application claims priority of European Patent Application 03 009 326.4 filed Apr. 24, 2003.

The present invention deals with an instrument system for pedicle screws having an internal thread in their head which accepts a grub screw with an external diameter $D_1$ in the direction of its screw axis in order to fixedly clamp a connection part which projects into the head transversely to the screw axis, with a holder with projections engaging in a shape matched manner at the head of the pedicle screw and a screwdriver with a diameter $D_4$ being able to be set at the grub screw.

Pedicle screws with clamping screws in their heads are described in the patent EP-A-0669 109. The company Centerpulse Orthopedics Ltd., CH-6340 Baar, Switzerland, distributes a stabilisation system with pedicle screws and associated instruments for spinal vertebrae under the name DYNESYS®. On the attachment of implants to the spinal column, it has previously only been possible with restrictions to use access approaches with little invasion when the natural structures should be largely maintained (Prof. Wiltse transmuscular approach or paraspinal approach). The operation field had to be prepared to be free in part from the centrally disposed spines of the vertebrae. The positioning of pedicle screws and the subsequent connection to stiffening elements requires great experience and skill in the surgeon.

It is the object of the present invention to improve this state and to give the surgeon more security. This object is satisfied in accordance with the independent claim 1 in that at least two holders with a tubular part are provided, with the tubular part being supportable at the head of the pedicle screw; in that a centring part is present which is insertable instead of the grub screw and can likewise be screwed into the internal thread, can be gripped when the holder is put on and corresponds in its outer diameter D to the diameter $D_1$ of the grub screw in order to be able to pull off the same holder, or another holder, and to be able to again lead it as often as desired to shaped matched mating surfaces of the pedicle screw, with the tubular part having an internal diameter $D_2$ which is only a little larger than the diameter $D_1$ in order to position the grub screw with the screwdriver or the centring part guided by the tubular part at the head of the pedicle screw such that its threads engage in a non-jamming manner with the internal thread.

This arrangement has the advantage that a grub screw can be inserted into the tubular part as a clamping screw outside of the actual operation field and slides under its own weight, or pushed by the screwdriver, to the head of the pedicle screw and can be screwed in there, without an instrument being necessary which grips the grub screw and without a risk that the grub screw is unintentionally put down at another place in the operation field. Since the internal diameter $D_2$ of the tubular part is only a little larger than the outer diameter $D_1$ of the grub screw, the latter maintains the position in which it was inserted into the tubular part. The screwdriver finds its shaped match, for example, in a hexagon socket in the grub screw and the grub screw finds the thread in the head of the pedicle screw. A reliable "finding" of the threads is achieved when the internal diameter $D_2$ amounts to less than 1.3 times the outer diameter $D_1$ of the grub screw.

A centring part provides an important advantage which can be inserted in the meantime through the tubular part instead of the clamping screw and which can likewise be screwed into the thread of the head and projects outwardly beyond the tubular part in the elongate direction.

A centring part anchored in this manner allows the holder to be pulled off and to put on the same holder, or other holders, in a guided manner and without a direct view of the pedicle screw.

The pedicle screw can be positioned without a grub screw through a first holder by this measure, said holder having a corresponding tubular part into which a centring part can be inserted instead of the grub screw, with the centring part being able to be gripped at its projecting end in order to screw it tight at the head of the pedicle screw. The largest diameter D of the centring part is slightly larger subsequent to a short threaded part than the thread diameter in order to form a support shoulder, but is still smaller than the internal diameter $D_2$ of the tubular part. Such an anchored centring part allows a first holder to be pulled from the head of the pedicle screw and to position other holders with other functions to be placed as often as desired onto the head of the pedicle screw without a direct view. A first holder can thus, for example, be conceived as a powerful screw-in tool which is supported in a shaped matched manner on later functional surfaces of the head and, after the screwing-in of the centring part, can be changed to another holder at a later point in time which is in turn pushed on until it contacts auxiliary surfaces of the head in a shape matched manner to allow the introduction and fixing of the grub screw after the pulling off of the centring part. This newly put on holder then guides the grub screw and the power screw driver and simultaneously makes a counter-torque possible on the fixing of the grub screw.

Independent claims 2 to 12, 14 and 15 represent advantageous further developments of the invention. The centring portion therefore makes the change of holders with different functions possible, without the contact to the head of the pedicle screw being lost.

Such a centring part can be rigid. A flexurally elastic design is even more favourable which, by its yielding, prevents large forces arising at the pedicle screw on the deflection of the screwed-on centring part despite its large lever length. Moreover, the centring parts can also be bent away so far that other devices, e.g. image converters/X-ray devices, can be used.

If the central region in the elongate direction is made elastic so that an angular deviation in the central region of, for example, 20° is possible in the central region, then a holder guided at the centring part can also be moved toward the head of a non-visible pedicle screw in an arc and can displace the covering tissue in a gentle manner. One possibility of producing the required elasticity in the central region consists of using a flexurally elastic material for the central part and/or of reducing the cross-section such that no unpermitted bending stresses occur. A further possibility consists of designing the central part as a multiple wire or as a helical spring in order to achieve a necessary elasticity.

To simplify the guiding of the centring part on the placing on of a holder, it is advantageous for the centring part to have circular cross-sections and jacket lines with gentle, stepless transitions.

If a first tubular holder is provided with a clamping apparatus which blocks a centring part screwed into the pedicle screw in the axial direction, for example by clamping, this combination can be used as a positioning instrument for the pedicle screw. The centring part is mounted onto the pedicle screw outside the human body and the position of a subsequently mounted holder is secured in the axial direction in that it is tensioned with respect to the centring part in order subsequently to screw in the pedicle screw with the holder. After the release of the clamping, the holder used as the setting instrument can be pulled of, because the surfaces of the pedicle screw contacting it in a shape matched manner should, for example, be otherwise used, and another holder can be guided along the centring part to the head of the pedicle screw. Such another holder can, for example, be a holder with a tubular part which has, at the end facing the pedicle screw, a projecting shoe with a deflection arc as a deflection device for a band or cable pulled through the screw head as a connection part and, at the other end of the tubular part—that is outside the actual operation field—with respect to the rotation of the tubular part a shape matched coupling surface for a cable tensioner which supports the cable tensioner in the direction towards the pedicle screw. This arrangement makes a pre-tensioning outside the actual operation field possible and thus manages with smaller dimensions for the access paths. Cable tensioners which are suitable for such an application are described in the patent EP-A-1103225. Since such cables, which are brought to a pre-determined pre-tension force by the cable tensioner prior to their fixing by the clamping screw, also have a certain flexural strength, it is advantageous to design the deflection arc with a radius larger than 3 mm. In this manner, no flexural torque which is too large arises at the pulled-through cable in the passage of the screw head and thus also no friction, which is too large, which could decisively falsify the measurement result of the applied pre-tension.

For pedicle screws of the aforesaid product DYNESYS®, the following operation sequence can for example be carried out with the instrument system described above when positioning in two adjacent vertebrae without the contact to the respective pedicle screw being lost:

1st Pedicle Screw a1) Screwing in and anchoring of a centring part on the head of the pedicle screw outside the operation field. Mounting a first holder until it lies on the head in a shape matched manner and securing—even better pre-tensioning—of the holder at the centring part in the axial direction. Screwing of the pedicle screw into the body of the vertebra.

b1) Releasing of the axial security and pulling off the holder; the centring part remains in place.

c1) Pulling of a cable through the screw head of the pedicle screw using forceps-like instruments not described here, with an orientation, and possible guiding, being possible at the centring part.

d1) Mounting a second holder with a tubular part along the centring part, with the second holder contacting into two side notches of the screw head in a shape matched manner.

e1) Removing the centring part by releasing the screw connection and by pulling it off and instead first inserting a grub screw and subsequently a screwdriver into the tubular part to fasten the cable finally by screwing in the clamping screw. The screwdriver can have an indicator for the torque with a corresponding measurement device for this purpose. Pulling off the powered screwdriver.

2nd Pedicle Screw a2) Analogue to a1) Putting on the first holder.

b2) Analogue to b1) i.e. a centring part remains in the screwed in pedicle screw.

Intermediate Steps:

Determining the spacing of the 1st and 2nd pedicle screws under a pre-determined spreading force to define the required length for a spacer to be pushed onto the cable. (A parallel application with the same application date has been filed for this device). The spreading instrument can be oriented on the first pedicle screw for the positioning at the screwed-in centring part of the second pedicle screw and at the cable.

Establishing of the pre-determined spacer length by cutting off the excess and pulling the pressure spacer onto the cable until the spacer abuts the 1st pedicle screw.

3rd Pedicle Screw c2) Analogue to c1) Pulling in the cable.

d2) Analogue to d1) Putting on a further holder, with a tubular part, but which additionally has a projecting shoe with a deflection arc and at the other end, i.e. outside the actual operation field, a shape-matched reception for a cable tensioner.

e2) Applying so much pre-tension with the placed-on cable tensioner until the spacer contacts both pedicle screws at its provided contact surfaces. Removing the centring part and instead inserting a grub screw and the screwdriver through the tubular part, producing an intended pre-tension with the cable tensioner and tightening the grub screw with the screwdriver at the cable at this pre-tensioning force at a pre-determined torque to secure the cable, with the counter-torque being able to be simultaneously absorbed with the belt tensioners via the shape matched reception.

If a further pedicle screw is provided at a subsequent vertebra, the procedure as for the 2nd pedicle screw can be followed. Generally, all pedicle screws can be positioned with the first holder as the first step. It is then all the more important that the centring parts each remain screwed into the pedicle screws. For each further pedicle screw to be inserted, its position can be estimated more easily at the already projecting centring elements.

Since with this instrument system, the holders have a tubular part which is coordinated with the alignment of the grub screw as regards its internal diameter and since projecting centring parts can be fastened in the heads of the pedicle screws through the holders instead of the grub screws, the contact to the inserted pedicle screw can even be maintained with a non visible, i.e. smaller, operation field.

The invention will be explained in the following with reference to embodiments. There are shown.

Figure 1:
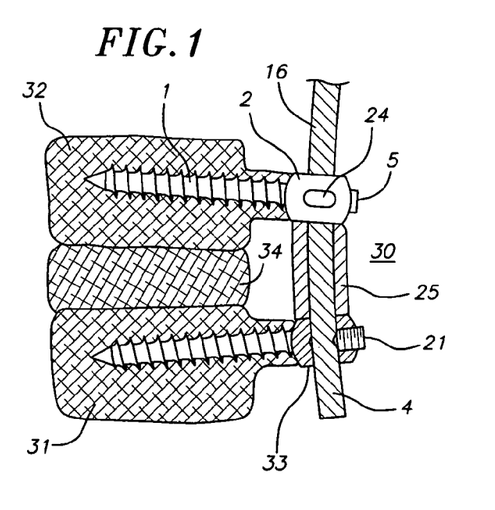
FIG. 1 schematically, two adjacent vertebrae in which, in accordance with the aforesaid EP-A-0669101, pedicle screws have been screwed which are connected to one another at pre-tension via a cable and via a pressure spacer.
Figure 2:
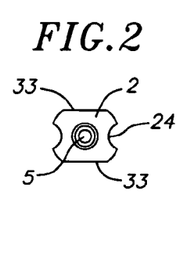
FIG. 2 corresponds to a plan view of the screw head of a pedicle screw of FIG. 1.

In FIGS. 1 and 2, a completely installed support element 30 is shown between two adjacent spinal vertebrae 31, 32 which is installable with an instrument system in accordance with the invention. The two pedicle screws 1 have a head 2 which is spherical and has in each case at two opposite sides flattened end faces 33 which form support surfaces for a cylindrical pressure spacer 25. Transversely to the end faces 33, an elastic, pre-tensioned cable 16 is drawn through the pressure spacer 25 in a bore and is held in each case by a grub screw 5 in the screw head 2. The grub screw 5 lies on the screw axis 21 of the pedicle screw. Notches 24 are applied to the side surfaces of the head 2 and a holder 6b (FIG. 6) can move into these to form a corresponding counter torque on the tightening of the grub screws 5 with a power screw driver 10.

The embodiment of a first holder 6a and its interaction at the head 2 of a pedicle screw 1 with a centring part 12 and with a clamping screw designed as a grub screw 5 is shown in the FIGS. 3, 4, 6 and 8. The holder 6a consists of a front part 26 which is designed as a tubular part 8 and ends in a mouth 27 which is supported on the head 2 of the pedicle screw 1 and engages around the free end faces 33 to generate a sufficiently large torque for the screwing in of the pedicle screw 1. A centring part 12 is anchored in the inner thread 3 of the head 2 at a threaded part which corresponds to the external thread 9 of a clamping screw designed as a grub screw 5, but is substantially shorter, to be able to later pull in a cable 16 even with a centring part 12 screwed in and sitting on with a diameter D.

The grub screw 5 has a largest diameter $D_1$ and a hexagon socket 39 for the powered screwdriver 10. The internal diameter $D_2$ of the tubular part 8 is only as large as that of a further holder 6b (FIG. 6) which is suitable as a guide on the introduction of the clamping screw 5.

The centring part 12 is therefore coordinated with its diameter D to the internal diameter $D_2$ of the tubular part 8 of both holders 6a, 6b, 6c, 6d, since it has to be longitudinally displaceable in both holders to be able to swap the holders for one another with a screwed-in centring part 12 and, on the other hand, to be able to move in the centring part 12 with a first holder 6 put on and to screw it securely into the internal thread 3 at the head.

Figures 5, 6, 7, 8, 9:
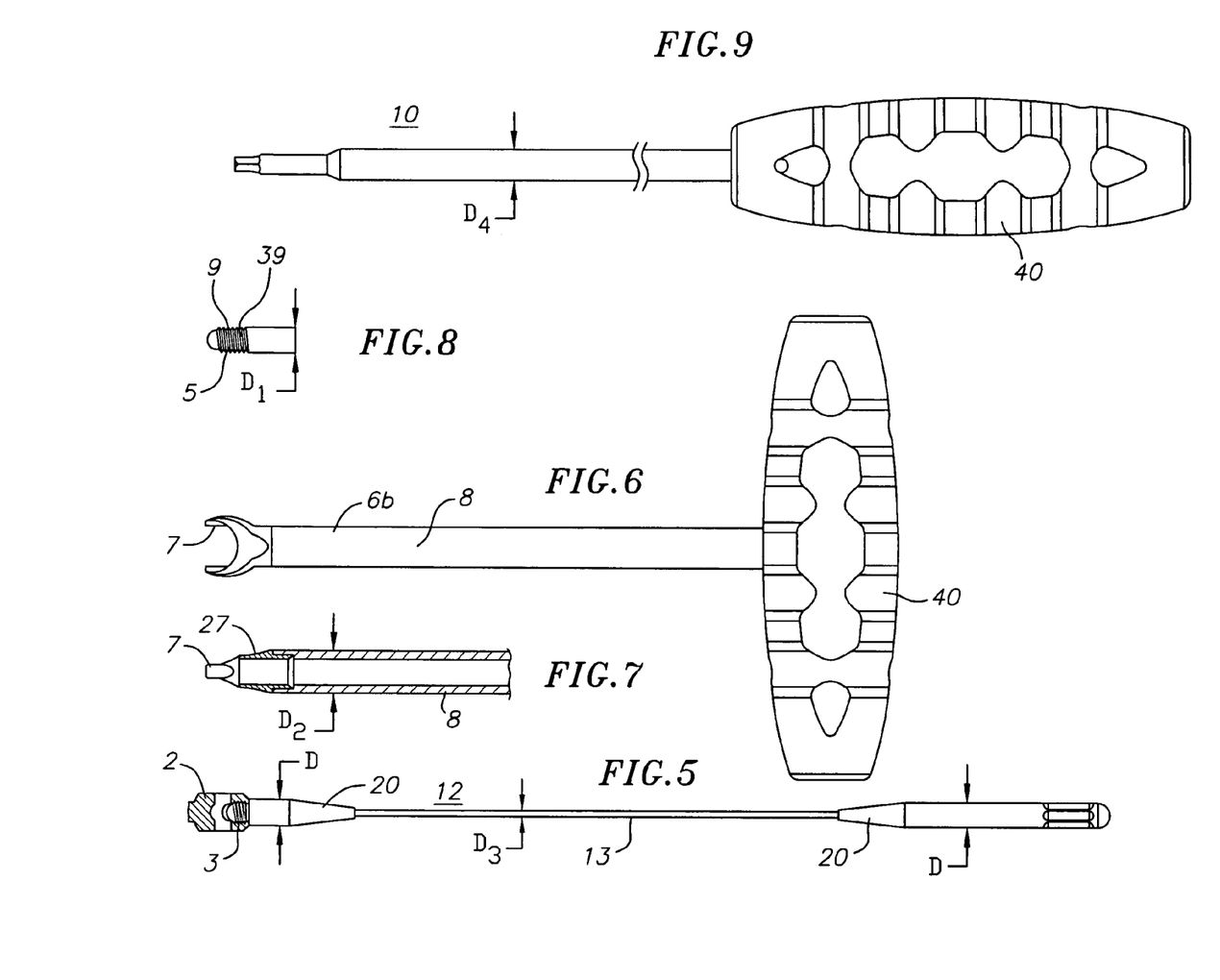
FIG. 5 schematically, a further centring part which is screwed into the head of a pedicle screw.
FIG. 6 schematically, a second holder which engages with projections in notches at the head of a pedicle screw.
FIG. 7 the lower part of the holder in FIG. 6, rotated by 90° in section.
FIG. 8 a clamping screw which is designed as a grub screw.
FIG. 9 a screwdriver for a grub screw in accordance with FIG. 8.

The front part 26 of the first holder 6a is fixedly screwed into a handle part 28 in which the tubular shape with diameter $D_2$ continues. A peripheral transverse groove 15, into which a lever 11 forked at the front projects in order to lock the screwed-in centring part 12 axially with a predetermined axial force, is applied in the region of the handle 28 to the centring part 12, whose central region 13 will be looked at in detail later. The function which this fixing element 14 exerts could likewise be realised with a radially moving in adjusting screw whose front edge is made in a conically tapering manner. Without the transverse groove 15, a clamping by a radially screwed in screw would be sufficient. In the present case, the lever 11 fixed by an axle 29 is provided with a contour 38 onto which a tappet 35 acted on by a compression spring 36 presses. The centring part 12 is latched in the position drawn. On turning back the lever 11, the front part of the contour 38, which corresponds to an arc of a circle piece about the axle 29, moves onto the tappet and into a region which is perpendicular to the axle 29 with respect to the tappet 35 such that the centring part 12 is freed and the first holder 6a can be released from the head 2 and can be removed, while the centring part 12 remains in the head. A plug 37 closes the bore which is necessary to introduce compression springs 36 and a tappet 35. The centring part 12 in FIG. 5 is designed in its central range 13 as a flexural spring with a diameter $D_3$ which is reached in each case via a conical transition piece 20. This central part 13 can be deflected elastically, for example, by up to 20° or more. The conical transition pieces 20 prevent the central part 13 from catching on any edges despite the deflection.

Figure 3:
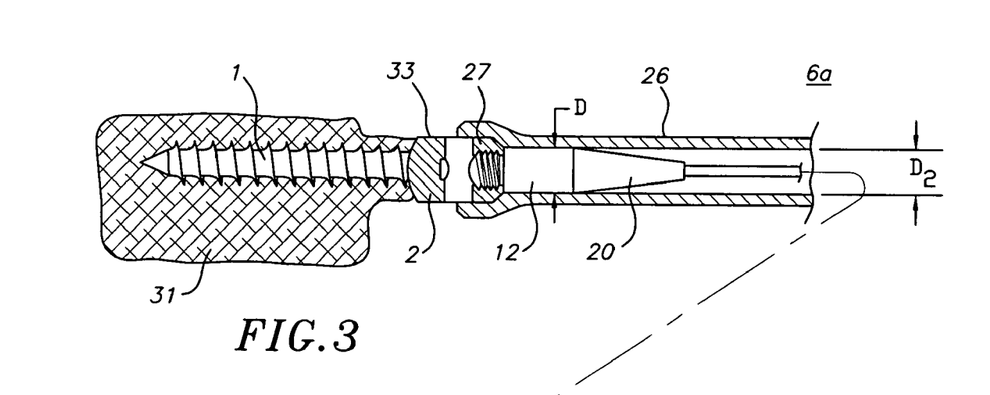
FIG. 3 schematically, the lower part of a first holder in accordance with the invention which forms a screw-in tool for a pedicle screw with a centring part.
Figure 4:
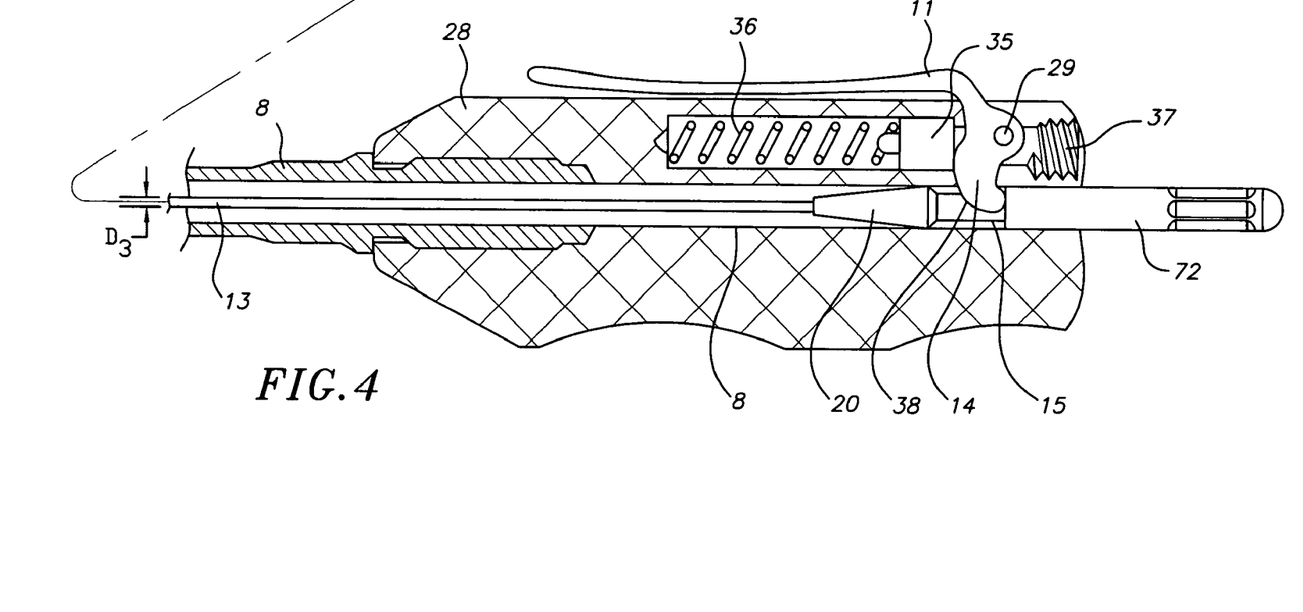
FIG. 4 schematically, an upper part with respect to the arrangement of FIG. 3 in which an axial securing of the centring part in the holder is shown.

A further holder 6d, analogue to the holder 6a in FIGS. 3 and 4, is shown with a centring part 12 with reference to FIGS. 18 to 21. Since it is a first holder 6d, which is used as a positioning instrument, the centring part 12, which should remain in place on the later removal of the holder, can initially be screwed to the pedicle screw and the holder 6d can subsequently be pushed on. In this case, the centring part 12 does not have to be pushed through the holder. The holder 6d, which likewise has a tubular part 8 with a mouth 27, has an extended handle part 28 with a clamping screw 73 projecting in the longitudinal axis which is supported at the handle part 28 at its outwardly engageable head 72 and projects with a tension thread 77 up to and into an internal thread 76 at the end of the centring part 12. The centring part 12 has at the other end a thread 61 with a subsequent shoulder with which it is wedged against the head 2 of a pedicle screw on the screwing in of the thread 61, whereas the tension thread 77 lies on the inner thread 76 without wedging and is therefore always released as the first thread when the clamping screw 73 is turned back. The clamping screw 73 itself is blocked by the friction of its head 72 against the handle part 28. It is understood that the thread 77 of the clamping screw 73 is made in the same direction as the thread 61 of the centring part 12.

The clamping screw 73 has two special features which can be used very generally for manually actuated screws in the art. To prevent an overloading of the threads 77, 76 during tensioning, the head 72 is kept so small and is provided with an asymmetric profile such that only small torques can be applied and such that larger torques can be applied for the release than for the tensioning by hand due to the asymmetry.

Figure 21:
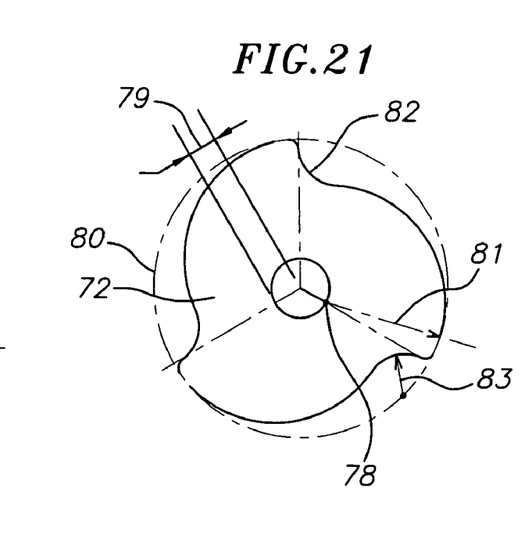
FIG. 21 schematically, an enlarged view of the end face of the clamping screw of FIG. 20 at which the contour of the head is visible.

FIG. 21 shows such an asymmetric profile. For the specific case of a clamping screw 73 with a head 72 which is provided at a pedicle screw for a centring part 12, the profile is included by an outer circle 80 with a diameter 15 mm. The profile is repeated at a spacing of 120° and is provided for a clamping screw 73 with a right hand thread. For this reason, the flanks which rise in the counter clockwise direction and via which the tension torque has to be applied, extend in a much shallower manner than the flanks rising in the clockwise direction for the releasing. When a maximum possible engaging force in the radial direction is assumed, this is achieved with a substantially smaller torque in the clockwise direction. In the example shown with an outer circle 80 with a diameter 15 mm, the flanks rising in the clockwise direction are produced by an arc of a circle with a radius 81 which merges tangentially into the outer circle 80 and has its centre at an inner circle with radius 79 which here amounts to 1.5 mm. The flanks rising in the counter clockwise direction are produced with an arc of a circle with a radius 83 which intersects the outer circle perpendicularly and has an amount of 2 mm such that a shoulder 82 of approximately 2 mm projects in the counter clockwise direction.

Generally, different angular spacings than 120° are also possible to arrive at a similar result with respect to torque limitation.

A further feature of the clamping screw 73 prevents this from accidentally releasing from the handle part 28 and, for example, falling to the floor from the sterile region. A projecting thread 74 is applied to the shaft of the clamping screw 73 and has to be screwed through a counter thread 75 in the handle part 28. Before the clamping screw 73 can be pushed deeper into the handle part. A few thread pitches thus prevent the clamping screw being released on its transport from the sterilisation into the operating theatre or being released from the handle part on a multiple use of the holder.

Figures 18, 20:
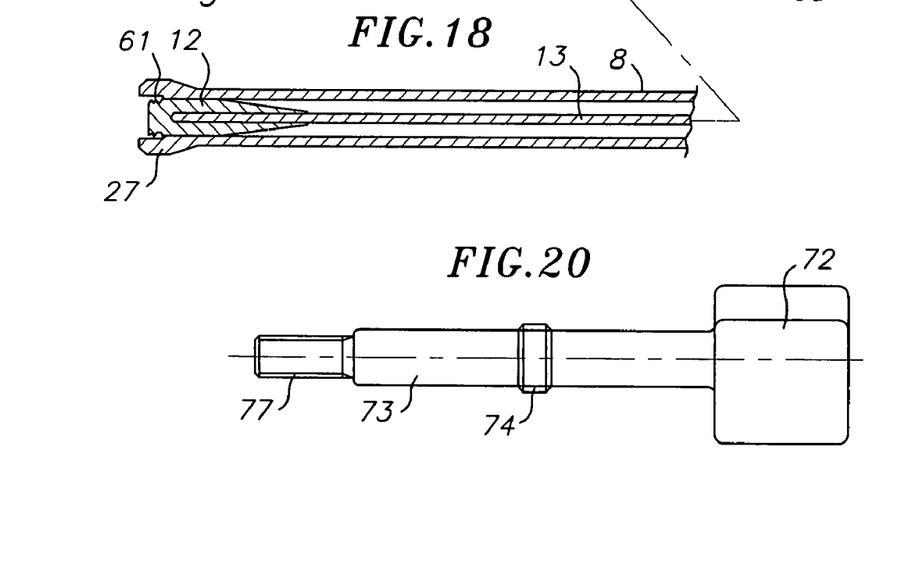
FIGS. 18 and 19: schematically, a further embodiment of a centring part and of a first holder which are combined as a screw-in tool analogue to FIGS. 3 and 4.
FIG. 20 schematically and enlarged, a clamping screw of FIG. 19 actuable by hand.
Figure 19:
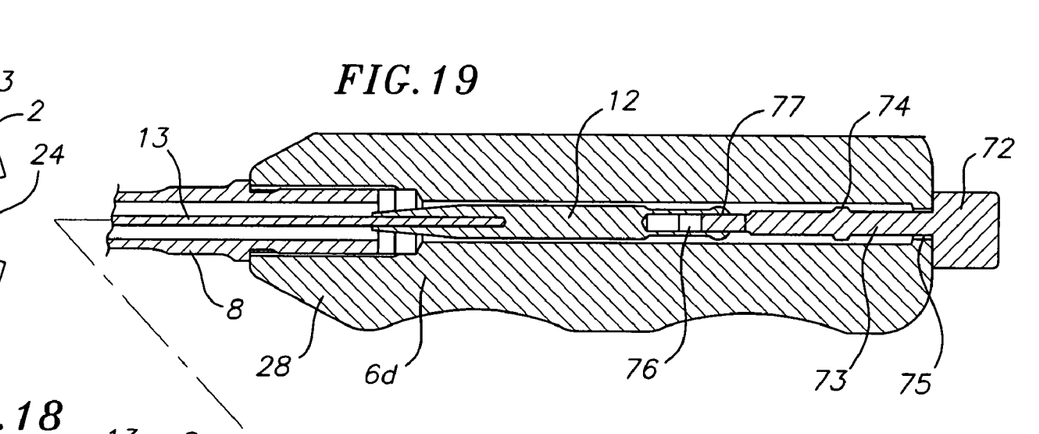
Figure 22:
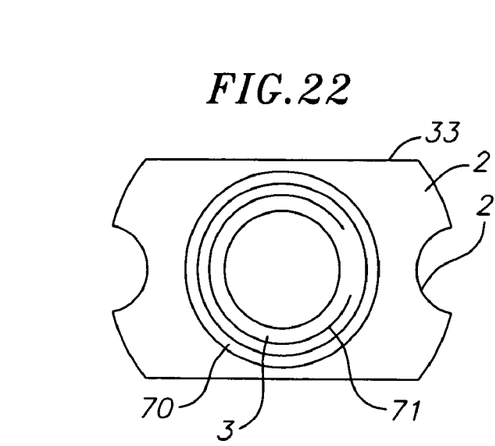
FIG. 22 schematically, at very high enlargement, the head of a pedicle screw in accordance with FIG. 2 which has a circular, planar support surface in the axial direction.

FIGS. 22 and 18 show a measure which allows an alignment of the tubular part 8 to be carried out with a circular ring-like support surface 70 in the axial direction at the head 2 of a pedicle screw when a corresponding mating surface is present at the mouth 27 of the holders 6a and 6d. The jaws of the mouth 27 projecting over the support surfaces 70 provide a lateral centring, that is for the congruence of the longitudinal axes of the pedicle screw 1 and the tubular part 8. The pedicle screw can thus not be moved like a joint in the mouth 27 despite the spherical surfaces at the head 2. Such an arrangement is not only of advantage for manually actuated positioning devices in accordance with the holders 6a and 6d, but can also be used in positioning tools of navigation systems (CAS, computer assisted surgery) when the position of the tip of a pedicle screw to a holder should be held precisely with a detectable reference position, always provided that this holder has a centring part 12 which remains in the head of the pedicle screw when the holder is released and removed from the screwed in pedicle screw. Such a centring part would then facilitate the subsequent manual operation steps in the sense of the invention with suitable further holders.

The function of a second holder 6b is described by the FIGS. 6, 7, 8 and 9 which can be pushed onto the head 2 of the 1st pedicle screw 1 after the moving out of the first holder 6a or 6d and is oriented at the centring part 12. Projections 7 move in a form matched manner into notches 24 at the head 2 of the pedicle screws. In this holder, a mouthpiece 27 is produced as a separate part from a high quality, wear-resistant steel and has subsequently been connected to the tubular part 8 which leads through a diagonally placed handle 40 to produce a counter torque on the tightening of the grub screw 5. The internal diameter $D_2$ of the tubular part 8 is smaller than 1.3 times, or even better smaller than 1.1 times, the outer diameter $D_1$ of the grub screw 5 in order to push this in a guided manner after the pulling out of the centring part 12 up to and onto the internal thread 3 in the head. The screwdriver 10 in FIG. 9 has a hexagon head which fits into the hexagon socket 39 of the grub screw 5. The outer diameter $D_4$ of the screwdriver 10 is selected such that the latter is guided in the tubular part 8 with the internal diameter $D_2$ and finds the inner hexagonal socket 39 of the grub screw 5. The front part of the screwdriver 10 with the diameter $D_4$ is made so long that it can be used with holders 6b and 6c to tighten inserted grub screws 5 with its handle 40.

Figure 10:
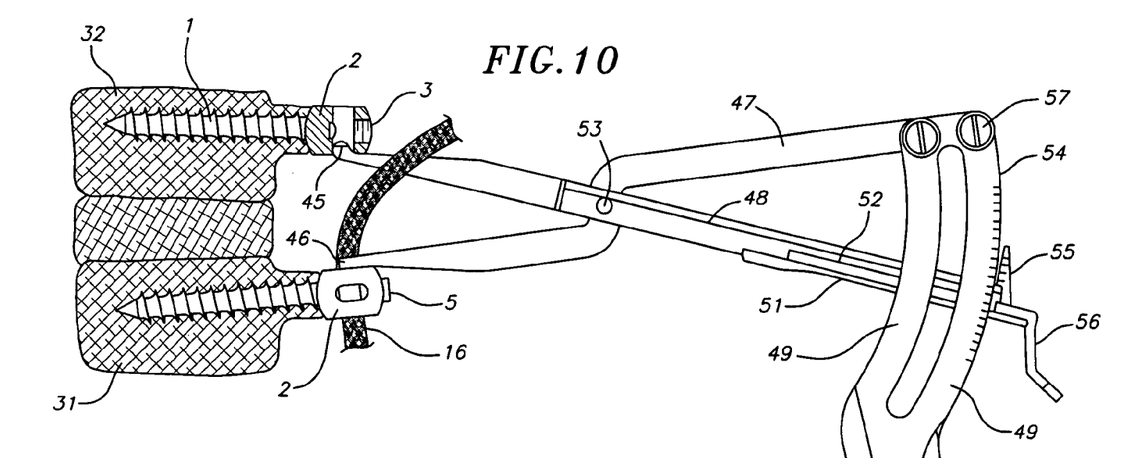
FIG. 10 schematically, a spreading instrument with which the spacing of two pedicle screws is determined under a pre-determined pre-tension force.
Figures 11, 12, 13, 23:
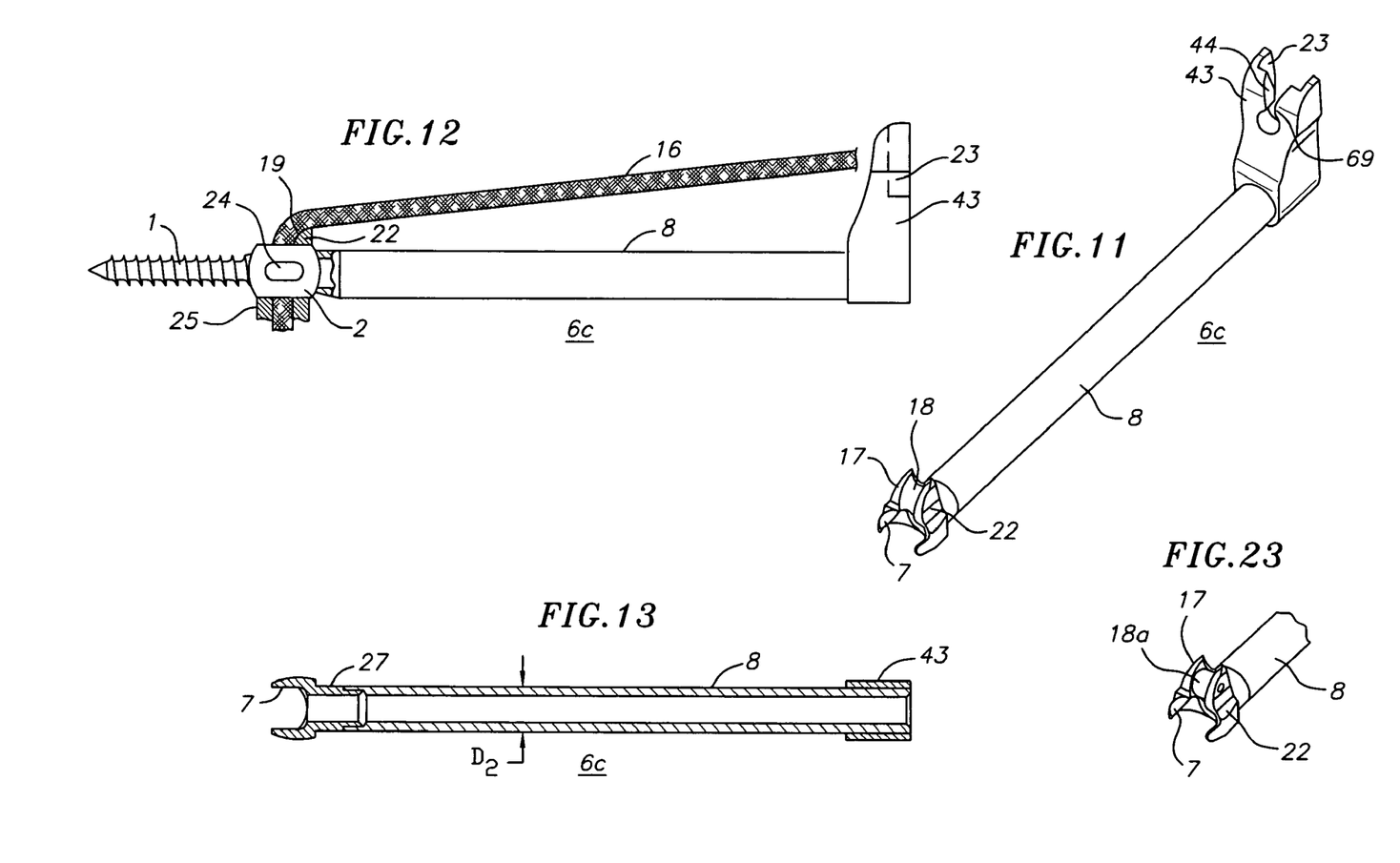
FIG. 11 schematically, a holder with a tubular part at which a deflection shoe has been set.
FIG. 12 schematically, a side view of the holder of FIG. 11 which is mounted onto the head of a pedicle screw.
FIG. 13 schematically, the holder of FIG. 12, rotated by 90° in section.
FIG. 23 schematically, the lower part of a holder analogue to FIG. 11, but which has a deflection roller instead of a deflection shoe.

A further holder 6c is shown with FIGS. 11, 12 and 13 which can be pushed on the second pedicle screw via a centring element 12. In a previous step, the second pedicle screw was positioned with the first holder 6a or 6d, this was subsequently pulled off and a centring element 12 remained. Subsequently, the spacing between the first and second pedicle screws was fixed at a specific distraction force by the spreading tool 42 shown in FIG. 10 and a suitable pressure spacer 25 was pulled onto the cable 16 and the cable was pulled through the head 2 of the second pedicle screw with the centring part 12 still mounted.

Only now is the further holder 6c pushed via the centring part 12 onto the second pedicle screw until its projections 7 engage in a shape matched manner into the notches 24, and then the centring part 12 is removed. A grub screw 5 can be inserted into the tubular part 8 and can be positioned at the head 2 of the pedicle screw using the screwdriver 10.

The further holder 6c likewise has a separately produced mouth 27 at which a shoe 17 is shaped which, when the holder is mounted, continues a passage bore through the head 2 with a deflection arc 18 by approximately 90°, with the deflection arc 18 being positioned at the passage bore continuously at its base 19. The deflection arc is made with a radius of curvature of more than 3 mm so that too much friction does not even arise by the deflection with a stiff cable 16 pulled through the passage bore. In a variant (see FIG. 23), the deflection arc 18 has been replaced by a moving deflection arc, that is by a roll 18a which is supported in laterally projecting jaws in the shoe 17.

The upper part of the holder 6c is made as a projecting arm 43 which has coupling surfaces 23 for a forceps-like cable tensioner (not shown). Such cable tensioners are separate, forceps-like tools having two limbs widening toward one another of which one is supported, for example, at the head 2 of the pedicle screw, while the other grips the cable and pulls it past the first limb. Cable tensioners are sold as tools for the previously mentioned product DYNESYS® of the company Centerpulse Orthopedics Ltd. Such a cable tensioner is positioned on the coupling surface 23 with the non-gripping limb after the cable 16 has been gripped by the gripping limb. The coupling surface 23 secures the non-gripping limb against turning about the tubular part 8 and simultaneously supports it in the direction towards the deflection arc 18.

A surgeon can therefore actuate the mounted cable tensioner with the one hand and produce a counter torque via the holder 6c and its projections 7 at the head 2 of the pedicle screw, while he can actuate the screwdriver 10 with the other hand in order to fix the cable when a pre-determined tensile stress has been reached in the cable 16.

In the coupling surface 23, a slot 44 is applied toward the deflection arc through which the cable 16 is introduced laterally when the cable tensioner is mounted. It is advantageous for the slot 44 to merge into a larger bore via a bottleneck 69 and for the bottleneck 69 to be dimensioned such that a cable has to be pushed into the bore under a force effect so that it is trapped in the bore and is guided out of the operation field without unintentionally being able to fall back into the operation field.

In FIG. 10, a spreading instrument 42 is shown in which two levers 47, 48 cross at a centre of motion 53 like a pair of forceps. At one of the levers 47, a crossbar 49 is attached with screws 57 which crosses the other lever 48 in an arc and ends in a handle 50. The first lever continues outwardly in two parts—in a rigid pointer part 52 and in a set-on flexural spring 51 which projects beyond the arc of the crossbar 49 with a thumb grip 56.

When the handle 50 is enclosed in the position drawn by four fingers of the right hand and the thumb is placed in the thumb grip 56, the apparatus can be spread by pulling the thumb.

The tip of the first lever 47 is of fork shape. This fork 46 contacts the head of the first pedicle screw and centres itself at the emerging cable 16. The tip of the other lever 48 ends in a laterally projecting semi-sphere 45 which is centred at the passage bore of the second pedicle screw. If now a spreading force is applied by pulling the thumb, the flexural spring 51 deforms toward the handle 50, whereas the rigid pointer part 52 only migrates further by so much at the arc of the crossbar 49 as the tips of the levers 47, 48 move apart.

A first scale 54 is attached to the arc-shaped part of the crossbar 49 and the outer spacing of the tips of the levers 47, 48 can be read off this.

A further, second scale 55 is connected to the thumb grip 56 which moves along with the movement of the flexural spring 51 and indicates, relative to the pointer part 52, at which pre-tension force the two tips are pressed apart. The purpose of the instrument consists of it being operable with one hand and of the length being determined for a pre-tension force predetermined between the vertebrae which forms a reference measure for a pressure spacer 25 to be inserted later. In accordance with the elastic properties of the material for the pressure spacer 25, the latter must be cut into shape in the untensioned state with respect to the reference measure such that it adopts a determined length after the installation and the tensioning of the cable.

A further application of the invention can be transferred in accordance with claims 13 to 15 and with FIGS. 14, 15, 16 and 17 to further embodiments of instruments which provide a screw 5' as a clamping screw with a projecting screw head 58, for example, a hexagon head. In a holder 66 in accordance with FIG. 15, for the internal diameter $D_2'$ of a tubular part 8, the outer diameter $D_4'$ of a screwdriver 10 is decisive which has a gripping device 59 for a screw head 58 at its matching hexagon socket 67 to hold the hexagon head screw 5' aligned towards the axis 62 of the screwdriver 10. The tubular part 8, which is only slightly larger in its internal diameter $D_2'$, for example by less than 1.2 times, then indirectly guides the clamping screw with its thread 60 via the screwdriver 10 up to and onto the internal thread 3 in the head 2 of the pedicle screw 1. The holder 66 is supported at its mouth 27 at the head 2 of the pedicle screw and engages with projections 7 in shape matched manner in notches in order to form a counter torque on the screwing in of the hexagon head screw 5' which fixes the cable 16 pulled in. The screwdriver 10 surrounds with a hexagon socket 67 the screw head 58, with the screw 5' being pressed into the hexagon socket 67 with a spring 64 which, oppositely disposed, engages beyond the lower rim of the screw head 58.

Figure 15:
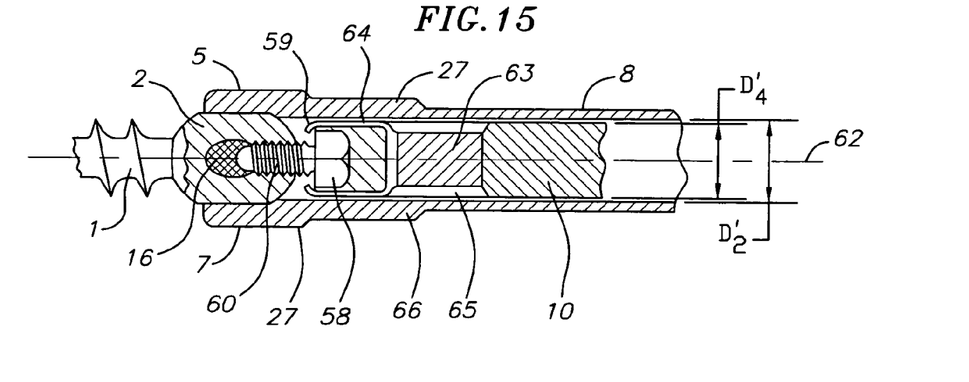
FIG. 15 schematically in section, the lower part of a second holder in the instrument set of FIG. 14 with a hexagon head screw which is held by a screwdriver and fixes a cable in the head of a pedicle screw.
Figure 16:
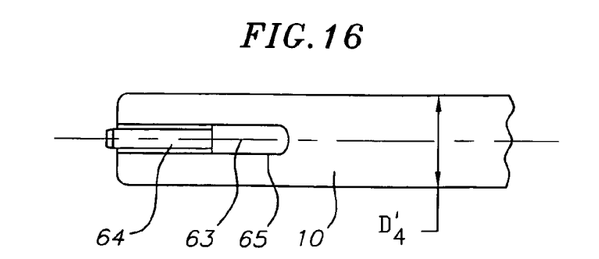
FIG. 16 schematically, a side view of the screwdriver of FIG. 15 rotated by 90°.
Figure 17:
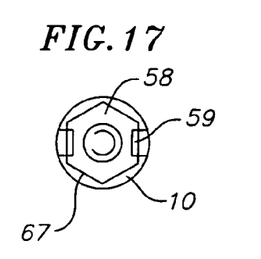
FIG. 17 schematically, an end face view of the screwdriver and screw of FIG. 15.

Due to the tight space situation, the spring is made in a C shape and has been pushed on from behind through a key slot 65 in the shaft of the screwdriver 10 and has been secured by a subsequent inserted key 63. The limbs of the spring 64 form a projection at their end which springs back on the insertion of the screw head 58 and holds the latter at its lower edge. The limbs themselves are each let into a groove so that they do not project beyond the diameter $D_4$ of the power screw driver.

Figure 14:
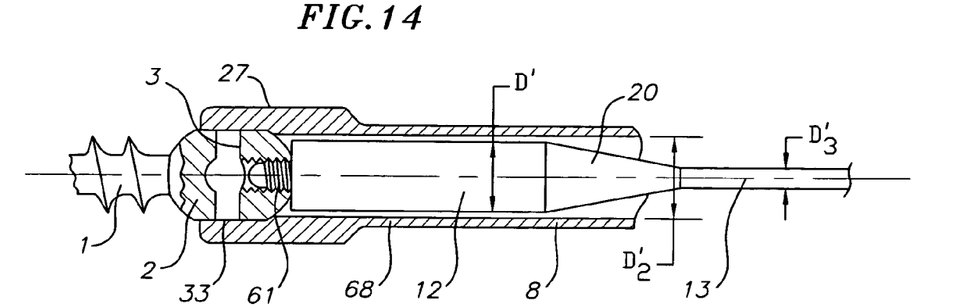
FIG. 14 schematically, the lower part of a first holder analogue to FIG. 3, but which is part of an instrument set for a clamping screw which is formed as a hexagon head screw.

In FIG. 14, a holder 68 matching FIG. 15 is shown with a centring part 12 whose diameter D' is slightly smaller than the diameter $D_2'$ of the holders 66, 68 so that these find their shape matched mating surfaces at the head 2 of the pedicle screw 1.

The centring part 12 is anchored with a thread 61 in the internal thread 3 at the head 2 of a pedicle screw 1. It has conical transitions 20 to a central part 13 which is made flexurally elastic with a smaller diameter $D_3$. The holder 68 is matched with its mouth 27 to the flattened end faces 33 of the head 2.

In addition to the two holders in FIGS. 14 and 15, there is a further holder which has a tubular part like the holder in FIG. 15 and likewise has the shoe 17 and a deflection apparatus 22 like the holder 6c (FIG. 8) and an arm 43 for a cable tensioner. It can generally be said of the instrument set in accordance with FIGS. 15 to 17 that the centring parts 12 have a largest diameter D' which is smaller than the diameter $D_2'$ of the tubular part 8. Other dimensions such as wall thicknesses of the tubular part 8 as well as further details and length dimensions of the instruments can correspond to the instrument set of the FIGS. 3 to 9, 11 to 13 and FIG. 21.

PARTS LIST 1 pedicle screw
2 head
3 internal thread
4 connection part
5 grub screw
5' screw
6 holder
6a first holder
6b second holder
6c further holder
6d holder
7 projection
8 tubular part
9 external thread
10 screwdriver
11 lever
12 centring part
13 central region
14 fixing element 15 transverse groove
16 cable
17 shoe
18 deflection arc
18a deflection roller
19 base
20 cone
21 screw axle
22 deflection apparatus
23 coupling surface
24 notch
25 pressure spacer
26 front part
27 mouth
28 handle part
29 axle
30 support element
31 spinal vertebra
32 spinal vertebra
33 end face
34 intervertebretal disc
35 tappet
36 spring
37 plug
38 contour
39 hexagon socket
40 grip
41 grip
42 spreading instrument
43 arm
44 slot
45 semi-sphere
46 fork
47 lever
48 lever
49 crossbar
50 handle
51 flexural spring
52 pointer part
53 centre of motion
54 1st scale
55 2nd scale
56 thumb grip
57 screws
58 screw head
59 gripping device
60 thread
61 thread
62 axle
63 key
64 spring
65 key slot
66 holder
67 hexagon socket
68 holder
69 bottleneck
70 support surface
71 countersink
72 head
73 clamping screw
74 thread
75 mating thread
76 internal thread
77 tension thread
78 internal circle
79 radius
80 external circle
81 radius
82 shoulder
83 osculating radius
D diameter
$D_1$ diameter, clamping screw, external
$D_2$ diameter, tubular part, internal
$D_3$ diameter, central part, centring part
$D_4$ diameter, screwdriver

The invention claimed is:

1. An instrument system comprising pedicle screws having an internal thread in their head, said thread accepting a grub screw with an external diameter $D_1$ in the direction of the screw axis to fixedly clamp a connection part which projects transversely to the screw axis into the head, further comprising: at least two holders with a tubular part, at least one of said holders being provided with projections configured for engaging in a shape matched manner at the head of the pedicle screws; a screwdriver with a diameter $D_4$ adapted to be positioned at the grub screw, the tubular parts of the at least two holders, being supportable at the head of the pedicle screws; and a centering part adapted to be screwed into the internal thread of the pedicle screws, instead of the grub screw, and to be gripped when one of said holders is mounted on the centering part corresponding in its external diameter D to the diameter $D_1$ of the grub screw with the tubular parts having an internal diameter $D_2$ which essentially equals with a loose-fit oversize, the diameter $D_1$ of the grub screw, in order to position the grub screw with the screwdriver or the centering part guided through the tubular part to the head of the pedicle screw such that threads of the grub screw engage with the internal thread of the pedicle screws in a non-tilted manner, wherein the centering part has a central region in the longitudinal direction which can be elastically deflected up to an angle of 20° or more away from the longitudinal axis.

2. An instrument system in accordance with claim 1, wherein the internal diameter $D_2$ amounts to less than 1.3 times the diameter $D_1$.

3. An instrument system in accordance with claim 1, wherein the internal diameter $D_2$ amounts to less than 1.1 times the diameter $D_1$.

4. An instrument system in accordance with claim 1, wherein the centering part has a lower diameter $D_3$ in its central region in order, as a flexural spring, to allow an envisaged deflection.

5. An instrument system in accordance with claim 1, wherein the centering part has substantially circular cross-sections and jacket lines with gentle, stepless transitions in the longitudinal direction following the central region.

6. An instrument system in accordance with claim 4, wherein the centering part has substantially circular cross-sections and jacket lines with gentle, stepless transitions in the longtitudinal direction following the central region.

7. An instrument system in accordance with claim 1, wherein one of said holders combines with a centering part to form a positioning apparatus for pedicle screws and comprises a fixing element blocking in an axial direction with respect to the centering part, said centering part in turn being screwed into the head of the pedicle screw.

8. An instrument system in accordance with claim 7, wherein the fixing element is in the form of a clamping screw which is supported at its head on the holder and engages in the axial direction into an internal thread at the rear part of the centering part.

9. An instrument system in accordance with claim 7, wherein the fixing element acts as a lever on a transverse groove of the centering element.

10. An instrument system in accordance with claim 1, wherein a tubular part includes a deflection apparatus for a band or cable pulled through the screw head a projecting shoe with a deflection arc and, at the other end of the tubular part, with respect to rotation, a shape matched coupling surface for a band or cable tensioner which supports the band or cable tensioner in the direction towards the pedicle screw.

11. An instrument system in accordance with claim 10, wherein the deflection arc has a radius of curvature larger than 3 mm along its base.

12. An instrument system in accordance with claim 10, wherein the shoe has a deflection roller instead of a deflection arc.

* * * * *